(12) United States Patent
Nakata et al.

(10) Patent No.: US 8,964,175 B2
(45) Date of Patent: Feb. 24, 2015

(54) COLORANT IDENTIFICATION METHOD AND COLORANT IDENTIFICATION APPARATUS

(71) Applicant: Horiba, Ltd., Kyoto (JP)

(72) Inventors: Yasushi Nakata, Kyoto (JP); Tomoko Numata, Kyoto (JP)

(73) Assignee: Horiba, Ltd. (JP)

( * ) Notice: Subject to any disclaimer, the term of this patent is extended or adjusted under 35 U.S.C. 154(b) by 0 days.

(21) Appl. No.: 14/079,954

(22) Filed: Nov. 14, 2013

(65) Prior Publication Data

US 2014/0132950 A1    May 15, 2014

(30) Foreign Application Priority Data

Nov. 14, 2012   (JP) ................... 2012-250469

(51) Int. Cl.
*G01J 3/44*       (2006.01)
*G01N 21/65*    (2006.01)
*G01N 21/64*    (2006.01)

(52) U.S. Cl.
CPC ............... *G01N 21/65* (2013.01); *G01N 21/64* (2013.01)
USPC ......................................................... 356/301

(58) Field of Classification Search
None
See application file for complete search history.

(56) References Cited

U.S. PATENT DOCUMENTS 6,545,755 B1 *   4/2003  Ishihama et al. .............. 356/301

FOREIGN PATENT DOCUMENTS

JP         2006-300808 A      11/2006

* cited by examiner

*Primary Examiner* — Tarifur Chowdhury
*Assistant Examiner* — Abdullahi Nur
(74) *Attorney, Agent, or Firm* — Cantor Colburn LLP

(57) ABSTRACT

Distribution is acquired for a reflectance spectrum and a fluorescence emission spectrum on a sample composed of color-image recorded matter. Then, on the basis of the distribution of the reflectance spectrum and the fluorescence emission spectrum, a single color portion is identified that is generated with one colorant selected from colorants of plural colors used in generating a color image. A control unit stores in advance Raman spectra of colorants of single color for each manufacturer. Laser light is projected onto the single color portion of the sample so that a Raman spectrum is measured. Then, the measured Raman spectrum is compared with the Raman spectra stored in advance so that the manufacturer of the colorant is identified and hence the colorant is identified.

8 Claims, 8 Drawing Sheets

F I G. 3A
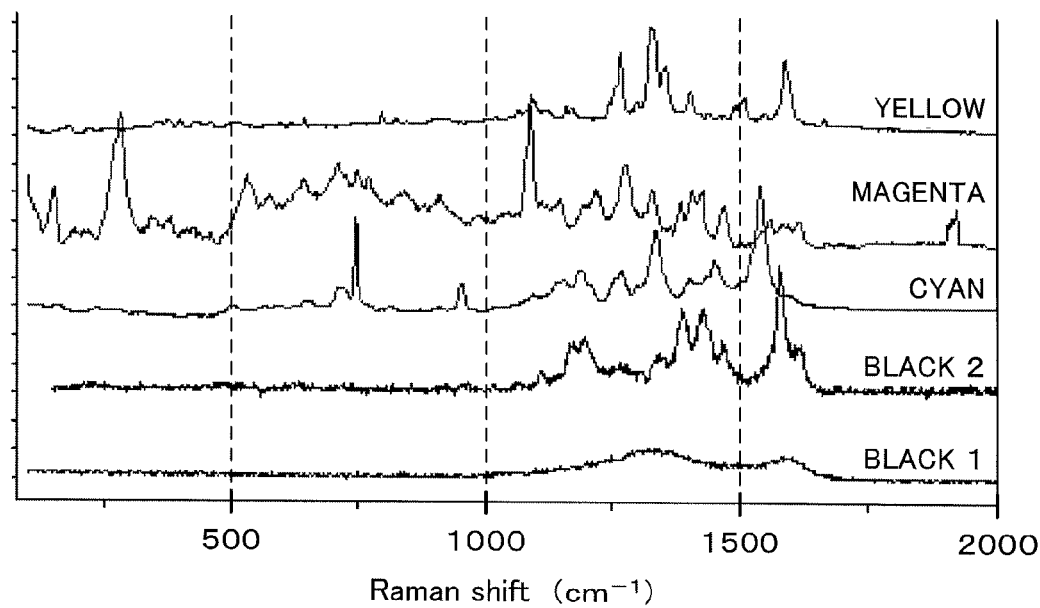
F I G. 3B
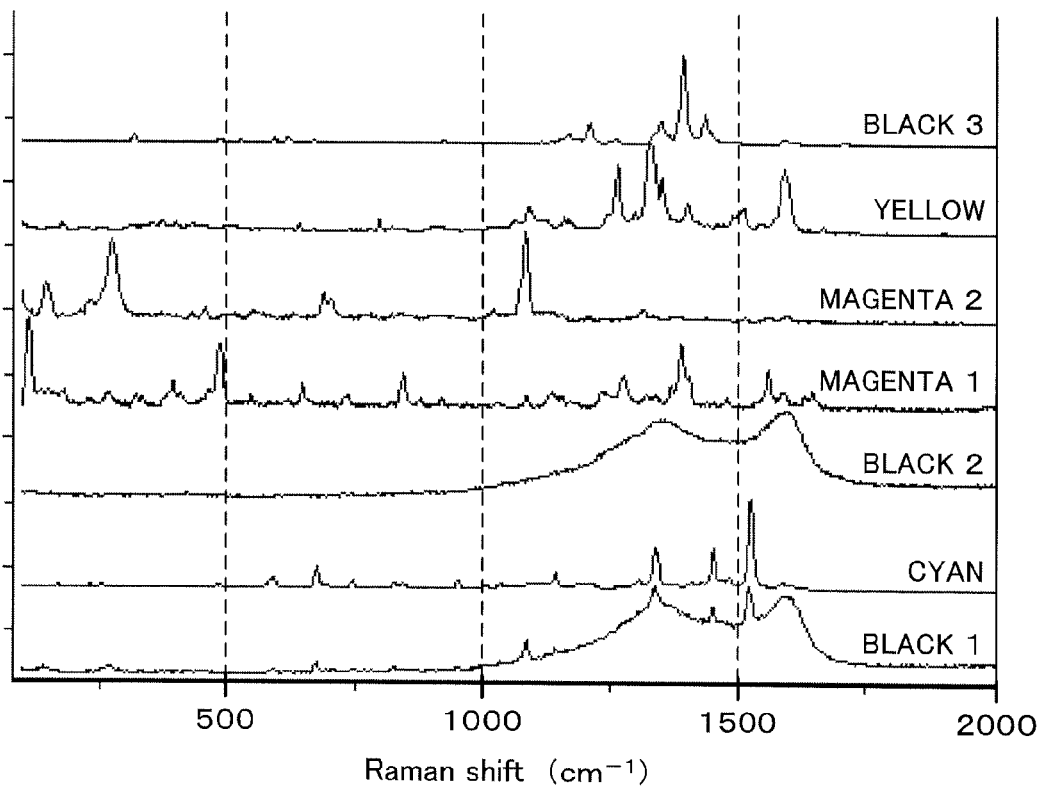

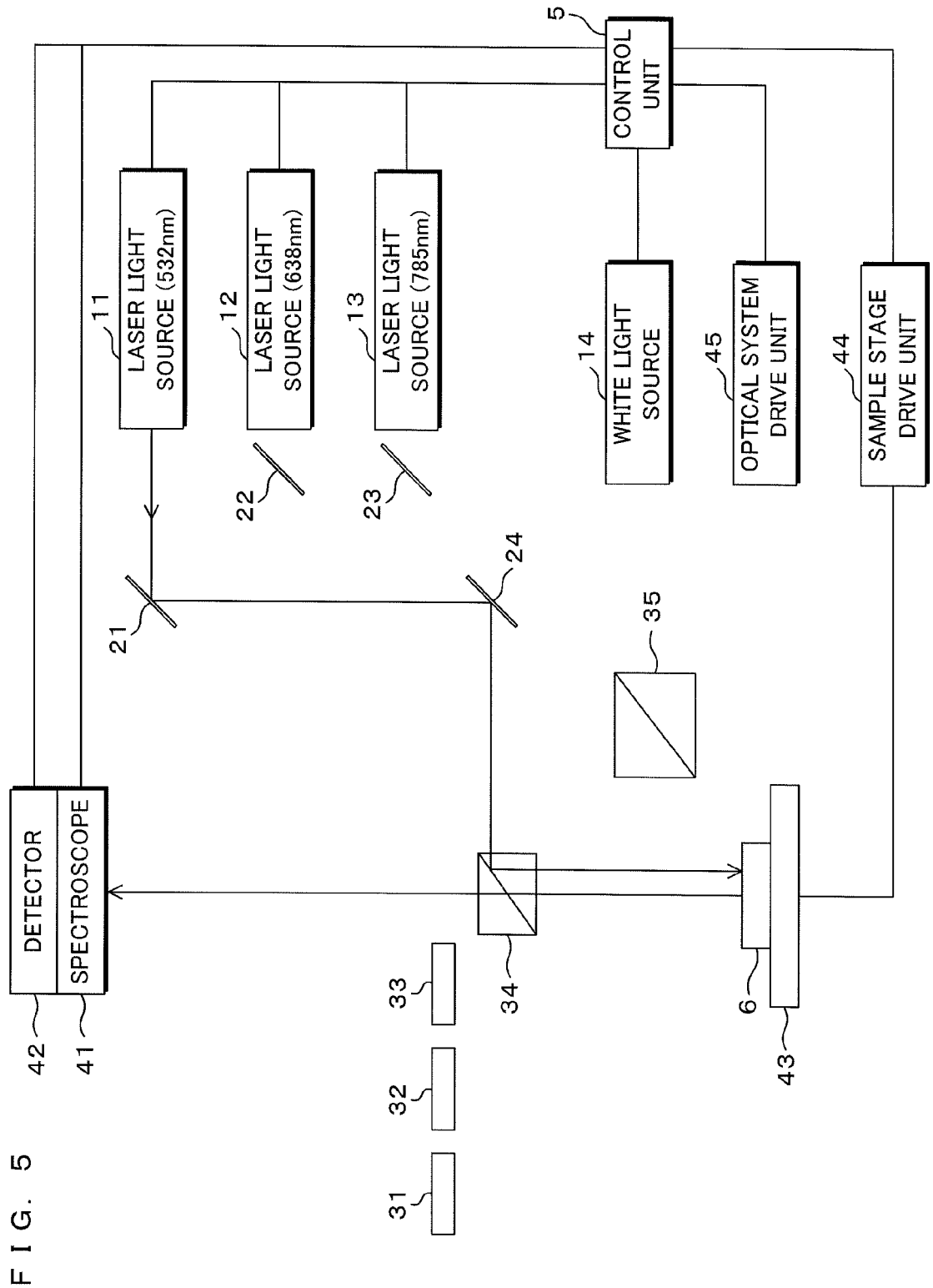
F I G. 5

COLORANT IDENTIFICATION METHOD AND COLORANT IDENTIFICATION APPARATUS

CROSS-REFERENCE TO RELATED APPLICATIONS

This Nonprovisional application claims priority under 35 U.S.C. §119(a) on Patent Application No. 2012-250469 filed in Japan on Nov. 14, 2012, the entire contents of which are hereby incorporated by reference.

BACKGROUND

1. Technical Field

The present invention relates to: a method for identifying by spectral analysis a colorant used in generating a color image; and a colorant identification apparatus.

2. Description of Related Art

With the advancement of image forming apparatuses, generation of image recorded matter such as a document obtained by recording an image on paper becomes easy. Thus, generation of unauthorized image recorded matter such as copied matter of a document recording secret information and forged matter of a banknote or securities also becomes easy like. Meanwhile, colorants such as ink and toner used in recording images have mutually different compositions in accordance with the difference of the manufacturers or the like of image forming apparatuses and colorants. Thus, when the colorant used in the image recorded matter is analyzed, the kind of colorant is allowed to be identified in correspondence to the difference of the manufacturers or the like of image forming apparatuses and colorants. Then, when the kind of colorant is identified, an image forming apparatus used in generation of unauthorized image recorded matter is allowed to be identified and this may contribute to investigation of the circumstances of generation of the unauthorized image recorded matter.

In the conventional art, Raman spectroscopy is used as a non-destructive method for analyzing a sample. Japanese Patent Application Laid-Open No. 2006-300808 describes that toner is adopted as a target of Raman spectroscopy. When Raman scattered light from colorants of mutually different kinds is measured, the obtained Raman spectra are different from each other. Thus, when the Raman spectrum of a colorant is investigated, the colorant is allowed to be identified.

SUMMARY OF THE INVENTION

A color image is generated by using colorants of plural colors. For example, an ink jet printer uses colorants of four colors consisting of cyan, magenta, yellow, and black in many cases. In the color image, colorants of plural colors are used in a mutually mixed manner in many portions. A Raman spectrum obtained from a color image in which colorants of plural colors are mixed is a spectrum obtained by superposing, with each other, Raman spectra obtained from colorants of individual colors. The mixing ratio of the colorants of plural colors varies arbitrarily and hence the Raman spectrum varies in correspondence to the mixing ratio. This causes a problem of difficulty in identifying the colorant from the color image.

The present invention has been devised in view of such a situation. An object thereof is to provide: a method for analyzing a colorant of particular color and thereby identifying the colorant from a color image; and a colorant identification apparatus.

A colorant identification method according to the present invention for identifying a colorant used in generating a color image is characterized by comprising steps of: storing in a database a fluorescence emission spectrum of a colorant of particular color and Raman spectra of plural kinds of colorants of a color which is equivalent to the particular color and of different compositions; projecting a monochromatic light onto a color image, then measuring fluorescence generated in each portion of the color image, and thereby acquiring distribution of a fluorescence emission spectrum in the color image; from the acquired distribution of the fluorescence emission spectrum, identifying a portion containing a fluorescence emission spectrum which is equivalent to the fluorescence emission spectrum of the colorant of the particular color stored in the database and thereby identifying a portion of the color image corresponding to the portion identified from the acquired distribution of the fluorescence emission spectrum; projecting monochromatic light onto the identified portion of the color image and thereby acquiring a Raman spectrum; and comparing the acquired Raman spectrum with the Raman spectra stored in the database and thereby identifying the colorant.

The colorant identification method according to the present invention is characterized by further comprising steps of: projecting white light onto the color image, then measuring reflected light from the color image, and thereby acquiring distribution of a reflectance spectrum in the color image; from the acquired distribution of the reflectance spectrum, identifying a region containing a reflectance spectrum corresponding to the particular color; and from a portion in the distribution of the fluorescence emission spectrum corresponding to the identified region, identifying a portion containing a fluorescence emission spectrum which is equivalent to the fluorescence emission spectrum of the colorant of the particular color.

The colorant identification method according to the present invention is characterized by further comprising steps of: storing in advance a wavelength of monochromatic light necessary for acquiring the Raman spectrum in the database in a manner of being in correspondence to each of the Raman spectra of the plural kinds of colorants; projecting monochromatic light of the wavelength stored in the database onto the color image and thereby acquiring a Raman spectrum; and comparing the Raman spectrum acquired by using monochromatic light of the particular wavelength with the Raman spectrum stored in correspondence to the particular wavelength in the database, and thereby identifying the colorant.

The colorant identification method according to the present invention is characterized in that the colorant of the particular color is one of colorants of plural colors used in generating a color image.

The colorant identification method according to the present invention is characterized by further comprising a step of identifying the colorant for each of the plural colors.

The colorant identification method according to the present invention is characterized by further comprising a step of measuring Raman scattered light generated in each portion of the color image and thereby acquiring distribution of a Raman spectrum in the color image.

A colorant identification apparatus according to the present invention for identifying a colorant used in generating a color image is characterized by comprising: a monochromatic light source; a storage unit storing a fluorescence emission spectrum of a colorant of particular color and Raman spectra of plural kinds of colorants of a color which is equivalent to the particular color and of different compositions; a fluorescence emission spectrum distribution acquisition unit projecting monochromatic light from the monochromatic light source onto a color image, then measuring fluorescence generated in each portion of the color image, and thereby acquiring distribution of a fluorescence emission spectrum in the color image; a first identification unit, from the distribution of the fluorescence emission spectrum acquired by the fluorescence emission spectrum distribution acquisition unit, identifying a portion containing a fluorescence emission spectrum which is equivalent to the fluorescence emission spectrum of the colorant of the particular color stored in the storage unit, and then identifying a portion of the color image corresponding to the portion; a Raman spectrum acquisition unit projecting monochromatic light onto the portion of the color image identified by the first identification unit and thereby acquiring a Raman spectrum; and an identification unit comparing the Raman spectrum acquired by the Raman spectrum acquisition unit with the Raman spectrum stored in the storage unit and thereby identifying the colorant.

The colorant identification apparatus according to the present invention is characterized by further comprising: a white light source; a reflectance spectrum distribution acquisition unit projecting white light from the white light source onto the color image, then measuring reflected light from the color image, and thereby acquiring distribution of a reflectance spectrum in the color image; and a second identification unit, from the distribution of the reflectance spectrum acquired by the reflectance spectrum distribution acquisition unit, identifying a region containing a reflectance spectrum corresponding to the particular color, wherein from a portion in the distribution of the fluorescence emission spectrum corresponding to the region identified by the second identification unit, the first identification unit identifies a portion containing a fluorescence emission spectrum which is equivalent to the fluorescence emission spectrum of the colorant of the particular color.

In the present invention, on the basis of the distribution of a fluorescence emission spectrum in a color image, a portion of the color image formed with a colorant of particular color is identified. Then, on the basis of the Raman spectrum measured in the identified portion, the colorant used in the color image is identified from among plural kinds of colorants of a color which is equivalent to the particular color and of mutually different compositions. Colorants of mutually different colors have mutually different fluorescence emission spectra. Thus, a portion formed with a colorant of a particular color is allowed to be identified. When the measured Raman spectrum is compared with the standard Raman spectra for plural kinds of colorants of the particular color stored in advance in the database, the colorant is allowed to be identified.

Further, in the present invention, from the distribution of the reflectance spectrum in the color image, a region containing the reflectance spectrum of the particular color is identified. Then, on the basis of the fluorescence emission spectrum in the identified region, a portion of the color image formed with the colorant of the particular color is identified. When both the reflectance spectrum and the fluorescence emission spectrum are utilized, the portion formed with the colorant of the particular color is allowed to be identified accurately.

Further, in the present invention, correspondence is established in advance between each of plural kinds of colorants and a wavelength of monochromatic light to be used for measuring the Raman spectrum. Then, the Raman spectrum measured by using monochromatic light of a particular wavelength is compared with the standard Raman spectra corresponding to the particular wavelength so that the colorant is identified. In mutually different kinds of colorants, in some cases, mutually different wavelengths of monochromatic light appropriately to be used for measuring the Raman spectrum are assigned. Thus, the colorant is identified on the basis of the combination of the wavelength of monochromatic light and the Raman spectrum.

Further, in the present invention, a portion is identified that is formed with a colorant of single color which is one of colorants of plural colors used in generation of a color image. Then, on the basis of the Raman spectrum measured in the identified portion, the colorant of single color is identified. Since a colorant of single color and a mixture of colorants of plural colors have different fluorescence emission spectra from each other, the portion formed with the colorant of single color is allowed to be identified. When the measured Raman spectrum is compared with the standard Raman spectra concerning the colorants of the single color, the colorant is allowed to be identified.

Further, in the present invention, each of the colorants of plural colors used in generating a color image is identified. The combination of identification results of the colorants of plural colors is obtained as information.

Further, in the present invention, distribution of the Raman spectrum in a color image is acquired. Thus, distribution of the colorant of a particular color is obtained.

In the present invention, the colorant used in a color image is identified easily. Thus, the present invention has an excellent effect of, for example, providing information useful in investigation of the circumstances of generation of unauthorized image recorded matter in which a color image is recorded.

The above and further objects and features of the invention will more fully be apparent from the following detailed description with accompanying drawings.

BRIEF DESCRIPTION OF THE SEVERAL VIEWS OF THE DRAWINGS

FIG. 3A is a characteristics diagram illustrating an example of a Raman spectrum;

FIG. 3B is a characteristics diagram illustrating an example of a Raman spectrum;

FIG. 5 is a block diagram illustrating a state of a colorant identification apparatus at the time of measuring a fluorescence emission spectrum;

DETAILED DESCRIPTION

The present invention is described below in detail with reference to the drawings illustrating an embodiment.

Figure 1:
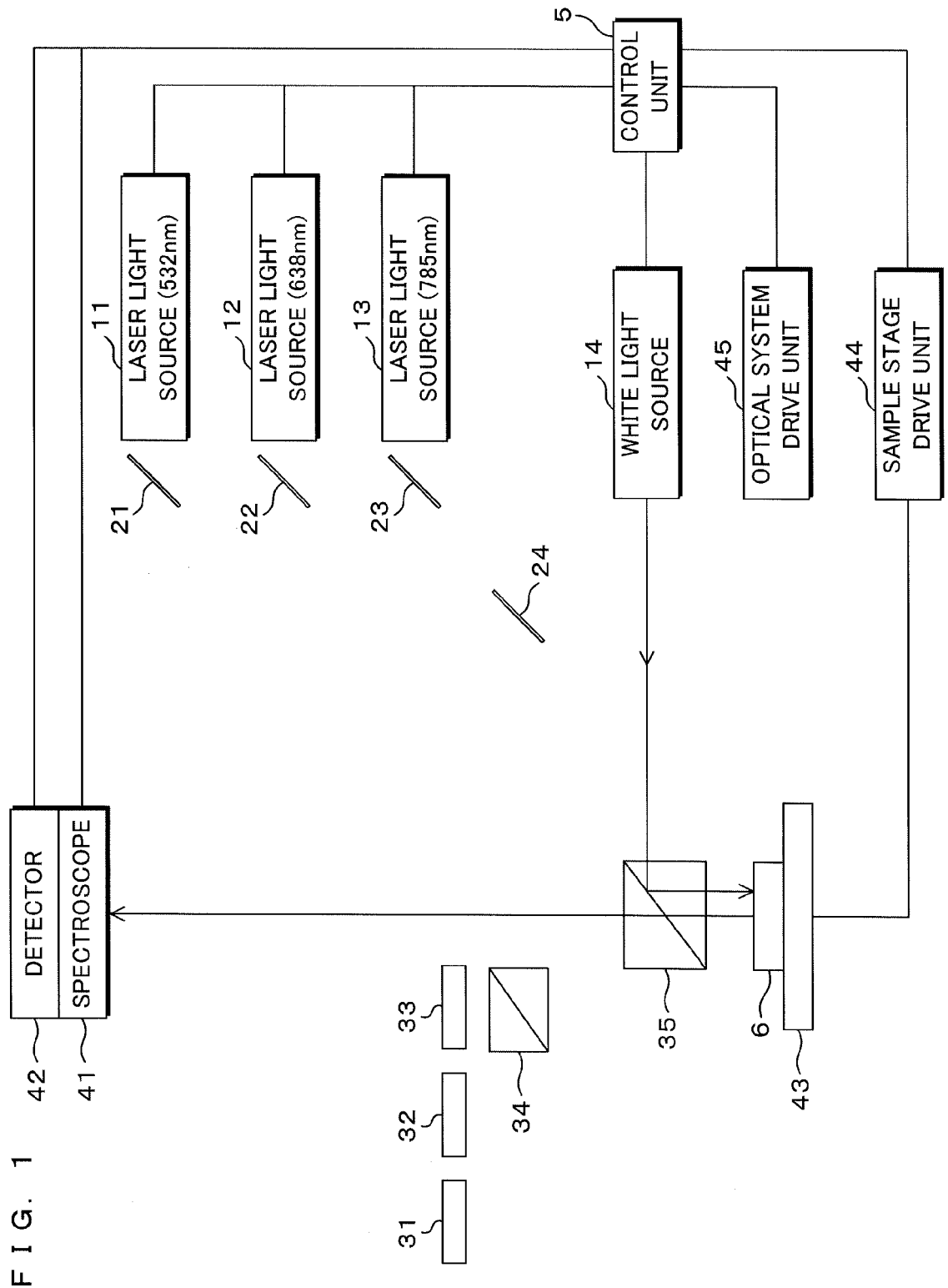
FIG. 1 is a block diagram illustrating a configuration of a colorant identification apparatus.

FIG. 1 is a block diagram illustrating the configuration of a colorant identification apparatus. The colorant identification apparatus, with adopting as a sample a color-image recorded matter generated by using colorants of plural colors, measures the reflectance spectrum, the fluorescence emission spectrum, and the Raman spectrum of the sample and then identifies the colorant on the basis of the measurement result. The colorant identification apparatus includes: a plurality of laser light sources 11, 12, and 13 having mutually different emission wavelengths; and a white light source 14. In the present embodiment, the emission wavelength of the laser light source 11 is 532 nm, the emission wavelength of the laser light source 12 is 638 nm, and the emission wavelength of the laser light source 13 is 785 nm. The white light source 14 is used for measuring the reflectance spectrum. The laser light sources 11, 12, and 13 are monochromatic light sources used for measuring the Raman spectrum. Further, the laser light source 11 having the shortest emission wavelength serves also as a light source used for measuring the fluorescence emission spectrum.

The colorant identification apparatus includes a spectroscope 41 and a detector 42. Further, at a position opposing the spectroscope 41, a sample stage 43 is provided onto which a sample 6 is placed. The spectroscope 41 receives the reflected light of the white light, the fluorescence, and the Raman scattered light generated by the sample 6 and then performs spectroscopy. The detector 42 is a multichannel detector and detects light of each wavelength obtained by the spectroscopy in the spectroscope 41 and then outputs a signal corresponding to the detected intensity of the light of each wavelength. For example, the detector 42 employs a CCD (Charge Coupled Device) photosensor. Here, the detector 42 may be a single channel detector employing an avalanche photodiode or a photomultiplier tube.

The colorant identification apparatus includes beam splitters 34 and 35. The beam splitters 34 and 35 are movable and any one of these is selectively arranged on the optical axis between the spectroscope 41 and the sample stage 43. FIG. 1 illustrates a situation that the beam splitter 35 is arranged on the optical axis. The white light source 14 is arranged at a position of projecting white light onto the beam splitter 35 arranged on the optical axis. In a state of being arranged on the optical axis, the beam splitter 35 reflects the light from the white light source 14 so as to project the light onto the sample 6 on the sample stage 43 and then transmits the reflected light from the sample 6.

The colorant identification apparatus includes movable mirrors 21, 22, and 23 and a fixed mirror 24. The mirrors 21, 22, and 23 are to be arranged at positions of individually reflecting the laser light from the laser light sources 11, 12, and 13. Then, any one of these is selectively moved to a position of reflecting the laser light from the corresponding laser light source toward the mirror 24. The mirror 24 is arranged at a position of reflecting the laser light from the mirror 21, 22, or 23 toward a beam splitter 34 arranged on the optical axis. In a state of being arranged on the optical axis, the beam splitter 34 reflects the laser light from the mirror 24 so as to project the laser light toward the sample 6 and then transmits the fluorescence and the scattered light generated by the sample 6. Further, the colorant identification apparatus includes Rayleigh cut filters 31, 32, and 33 cutting off light of wavelengths equivalent to those of the laser light from the laser light sources 11, 12, and 13. The Rayleigh cut filters 31, 32, and 33 are movable and any one of these is selectively moved to a position on the optical axis between the spectroscope 41 and the sample stage 43. In a state of being arranged on the optical axis, the Rayleigh cut filters 31, 32, and 33 cuts off the Rayleigh scattered light of the laser light from the laser light sources 11, 12, and 13 and transmits the Raman scattered light of the different wavelengths among the scattered light from the sample 6. Here, the colorant identification apparatus may include other optical components (not illustrated) such as other mirrors, lenses, and collimators.

The sample stage 43 is linked to a sample stage drive unit 44 constructed from a stepping motor and the like moving the sample stage 43 in horizontal plane directions. Further, the colorant identification apparatus includes an optical system drive unit 45 moving the mirrors 21, 22, and 23, the Rayleigh cut filters 31, 32, and 33, and the beam splitters 34 and 35. Further, the colorant identification apparatus includes a control unit 5 controlling the operation of individual parts of the colorant identification apparatus. The laser light sources 11, 12, and 13, the white light source 14, the spectroscope 41, the detector 42, the sample stage drive unit 44, and the optical system drive unit 45 are connected to the control unit 5. The laser light sources 11, 12, and 13 and the white light source 14 are controlled by the control unit 5 with respect to their ON and OFF. The spectroscope 41 is controlled by the control unit 5 with respect to the wavelength of the light to be processed by the spectroscopy for the purpose of detection in the detector 42. The detector 42 outputs a signal corresponding to the detected intensity of the light to the control unit 5. The control unit 5 receives the signal outputted by the detector 42 and then performs the processing of generating a spectrum on the basis of the wavelength of the light under the spectroscopy in the spectroscope 41 and on the basis of the detected intensity of the light indicated by the inputted signal. The sample stage drive unit 44 is controlled by the control unit 5 with respect to the position to which the sample stage 43 is to be moved. The optical system drive unit 45 is controlled by the control unit 5 with respect to the position to which each optical component is to be moved.

Figure 2:
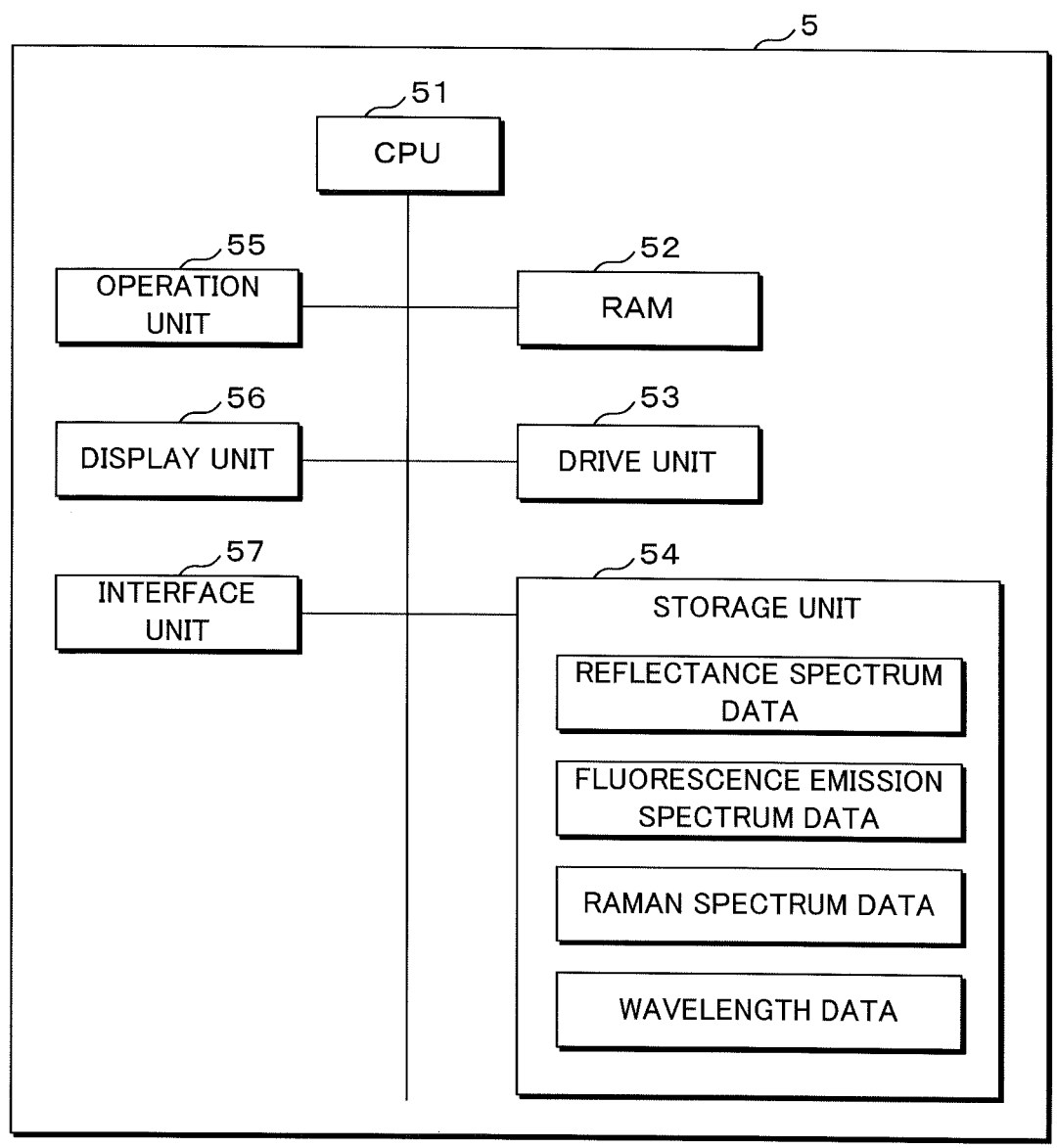
FIG. 2 is a block diagram illustrating an internal configuration of a control unit.

FIG. 2 is a block diagram illustrating the internal configuration of the control unit 5. The control unit 5 is constructed from a computer such as a personal computer. The control unit 5 includes: a CPU (Central Processing Unit) 51 performing computation; a RAM (Random Access Memory) 52 storing temporary data generated in the computation; a drive unit 53 reading information from a recording medium such as an optical disc; and a nonvolatile storage unit 54 such as a hard disk. The control unit 5 further includes: an operation unit 55 such as a keyboard and a mouse receiving operation from a user; a display unit 56 such as a liquid crystal display; and an interface unit 57. The interface unit 57 is connected to other parts of the colorant identification apparatus. The storage unit 54 stores a computer program necessary for the operation. When necessary, the CPU 51 loads the computer program from the storage unit 54 onto the RAM 52 and then, in accordance with the loaded computer program, executes processing necessary in the colorant identification apparatus.

The storage unit 54 is a database storing data necessary for identification of the colorant. The storage unit 54 stores reflectance spectrum data representing the spectrum of each color contained in a color image. The reflectance spectrum data contains data representing the reflectance spectrum of each of the colorants of plural colors used in generating a color image and contains, for example, data representing the reflectance spectrum of each of cyan, magenta, yellow, and black. Further, the storage unit 54 stores the fluorescence emission spectrum data representing the fluorescence emission spectrum of each of colorants of plural colors. For example, the fluorescence emission spectrum data contains data representing the fluorescence emission spectrum of each of cyan, magenta, yellow, and black. Further, the storage unit 54 stores the Raman spectrum data representing the Raman spectrum of each of colorants of plural colors for each colorant manufacturer.

FIGS. 3A and 3B are characteristics diagrams illustrating an example of the Raman spectrum. The horizontal axis in the figure indicates the Raman shift in the unit of wave number. FIG. 3A illustrates the Raman spectrum of a colorant fabricated by a particular manufacturer (referred to as company A, hereinafter). FIG. 3B illustrates the Raman spectrum of a colorant fabricated by another manufacturer (referred to as company B, hereinafter). Each figure illustrates the Raman spectra of colorants of cyan, magenta, yellow, and black. Two kinds of black are present in the colorants fabricated by company A, and three kinds of black and two kinds of magenta are present in the colorants fabricated by company B. As illustrated in FIG. 3, colorants of even the same color have mutually different Raman spectra when their manufacturers are different from each other. The Raman spectrum data contains also the data of the Raman spectra of colorants of the same manufacturer and the same color but mutually different kinds.

Further, the storage unit 54 stores wavelength data defining the wavelength of laser light to be used in the measurement of the Raman spectrum of the colorant of each color. When laser light is projected onto the colorant for the purpose of measurement of the Raman spectrum, fluorescence is generated by the colorant and then detected by the detector 42 together with Raman scattered light. The fluorescence detected at the time of measurement of the Raman spectrum disturbs the analysis of the Raman spectrum. Thus, the measurement of the Raman spectrum is preferred to be performed under a condition that the amount of generation of fluorescence is reduced. In the wavelength data, a suitable wavelength of laser light reducing the amount of generation of fluorescence in the measurement of the Raman spectrum of each colorant among the wavelengths of the laser light available in the colorant identification apparatus is recorded in a manner of being in correspondence to each colorant. Even for colorants of the same manufacturer, mutually different wavelengths of the laser light correspond to the colorants of mutually different colors, in some cases. Further, even for colorants of the same color, mutually different wavelengths of the laser light correspond to the colorants of mutually different manufacturers, in some cases.

Figure 4:
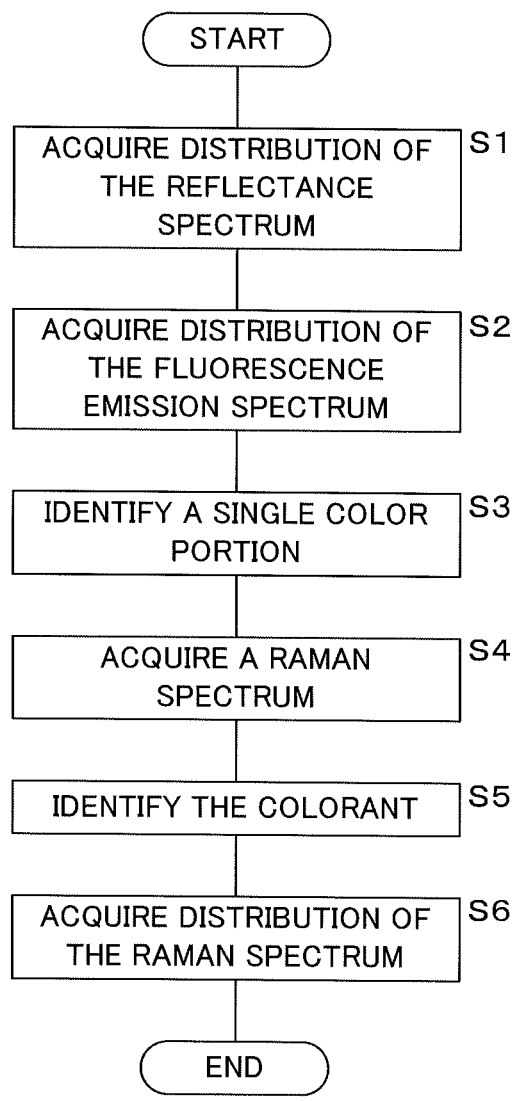
FIG. 4 is a flow chart illustrating a procedure of processing executed by a colorant identification apparatus.

Next, the operation of the colorant identification apparatus is described below. FIG. 4 is a flow chart illustrating a procedure of the processing executed by the colorant identification apparatus. In a state that the sample 6 composed of a color-image recorded matter is placed on the sample stage 43, the colorant identification apparatus projects white light onto the sample 6 and thereby acquires distribution of the reflectance spectrum on the sample 6 (S1). The control unit 5 controls the optical system drive unit 45 such that, as illustrated in FIG. 1, the beam splitter 35 is arranged on the optical axis between the spectroscope 41 and the sample stage 43. Then, the control unit 5 appropriately adjusts the wavelength range of the spectroscopy performed by the spectroscope 41, and then causes the white light source 14 to emit light. White light is projected from the white light source 14 onto the sample 6 and then the reflected light enters the spectroscope 41. In FIG. 1, the white light and the reflected light are indicated by arrows.

The detector 42 detects the light of each wavelength having undergone spectroscopy in the spectroscope 41 and then outputs a signal corresponding to the detected intensity of the light of each wavelength. In a mode that the detector 42 is composed of a single channel detector, the control unit 5 controls the spectroscope 41 so as to sequentially change the wavelength of the light detected by the detector 42 and then the detector 42 sequentially outputs a signal corresponding to the detected intensity of the light whose wavelength is sequentially changed. On the basis of the contents of spectroscopy by the spectroscope 41 and the signal from the detector 42, the CPU 51 generates a spectrum representing the relation between the wavelength and the intensity of the reflected light from the sample 6. Further, the control unit 5 controls the sample stage drive unit 44 so as to move the sample stage 43 horizontally and thereby projects white light sequentially onto each portion of the sample 6 and generates sequentially a spectrum of the reflected light from each portion of the sample 6. Further, the control unit 5 projects white light onto a portion of the sample 6 where a color image is not recorded, and then generates a spectrum of the reflected light. This provides the spectrum of the reflected light from an underlying portion where a colorant is not present within the color-image recorded matter. Here, the control unit 5 may store data representing the spectrum of the reflected light from the underlying portion, in advance in the storage unit 54. The CPU 51 divides the spectrum of the reflected light from each portion of the sample 6 by the spectrum of the reflected light from the underlying portion, and thereby generates a reflectance spectrum representing the reflectivity of each wavelength. Then, the CPU 51 establishes correspondence between the generated reflectance spectrum and each portion of the sample 6 and thereby acquires the distribution of the reflectance spectrum on the sample 6. The CPU 51 stores data representing the distribution of the reflectance spectrum in the storage unit 54.

Then, the colorant identification apparatus projects laser light onto the sample 6 and thereby acquires distribution of the fluorescence emission spectrum on the sample 6 (S2). FIG. 5 is a block diagram illustrating the state of the colorant identification apparatus at the time of measuring a fluorescence emission spectrum. The control unit 5 controls the optical system drive unit 45 such that, as illustrated in FIG. 5, the beam splitter 34 is arranged on the optical axis between the spectroscope 41 and the sample stage 43 and the mirror 21 is arranged at a position where laser light from the laser light source 11 is reflected toward the mirror 24. Further, when necessary, the control unit 5 adjusts the wavelength range of the spectroscopy performed by the spectroscope 41. The control unit 5 causes the laser light source 11 to emit light so that laser light of wavelength 532 nm is projected onto the sample 6. Then, fluorescence is generated by the sample 6 and then the fluorescence enters the spectroscope 41. In FIG. 5, the laser light and the fluorescence are indicated by arrows. As the light source used for measuring the fluorescence emission spectrum, a laser light source other than the laser light source 11 may be used. Nevertheless, since the wavelength of fluorescence is longer than the wavelength of the excitation light, in order to obtain a fluorescence emission spectrum having a larger amount of information, it is preferable to adopt as the light source the laser light source 11 having the shortest emission wavelength.

The detector 42 outputs a signal corresponding to the detected intensity of the fluorescence of each wavelength obtained by the spectroscopy. In a mode that the detector 42 is composed of a single channel detector, the control unit 5 controls the spectroscope 41 so as to sequentially change the wavelength of the fluorescence detected by the detector 42 and then the detector 42 sequentially outputs a signal corresponding to the detected intensity of the fluorescence whose wavelength is sequentially changed. While controlling the spectroscope 41 so as to change the wavelength of the fluorescence detected by the detector 42, the control unit 5 receives the signal corresponding to the intensity of the light detected by the detector 42. On the basis of the contents of spectroscopy by the spectroscope 41 and the signal from the detector 42, the CPU 51 generates a fluorescence emission spectrum representing the relation between the wavelength and the intensity of the fluorescence generated by the sample 6. Further, the control unit 5 controls the sample stage drive unit 44 so as to move the sample stage 43 horizontally and thereby projects laser light sequentially onto each portion of the sample 6 and generates sequentially a fluorescence emission spectrum from each portion of the sample 6. The CPU 51 establishes correspondence between the fluorescence emission spectrum in each portion of the sample 6 and each portion of the sample 6 and thereby acquires distribution of the fluorescence emission spectrum on the sample 6. The CPU 51 stores data representing the distribution of the fluorescence emission spectrum in the storage unit 54.

Then, the colorant identification apparatus identifies from the sample 6 a single color portion formed with only one of colorants of plural colors used in generation of a color image (S3). At step S3, the CPU 51 identifies from the distribution of the reflectance spectrum a region containing the reflectance spectrum of a single color. Specifically, the CPU 51 compares the measured reflectance spectrum with any reflectance spectrum of cyan, magenta, yellow, or black represented by the reflectance spectrum data stored in the storage unit 54 and thereby identifies a region containing a reflectance spectrum that agrees with the reflectance spectrum represented by the reflectance spectrum data within a given limit defined in advance. Then, from the portion corresponding to the region identified in the distribution of the fluorescence emission spectrum, the CPU 51 identifies a portion containing the fluorescence emission spectrum of a single color. Specifically, the CPU 51 compares the measured fluorescence emission spectrum with any fluorescence emission spectrum of cyan, magenta, yellow, or black represented by the fluorescence emission spectrum data stored in the storage unit 54 and thereby identifies a region containing a fluorescence emission spectrum that agrees with the fluorescence emission spectrum represented by the fluorescence emission spectrum data within a given limit defined in advance. At step S3, the colorant identification apparatus identifies a single color portion for each of the colorants of plural colors. That is, a single color portion of each of cyan, magenta, yellow, and black is identified. Here, at step S3, the CPU 51 may execute all the processing. Alternatively, operation performed by a user may be included like the user operates the operation unit 55 so as to specify a single color portion.

Figure 6:
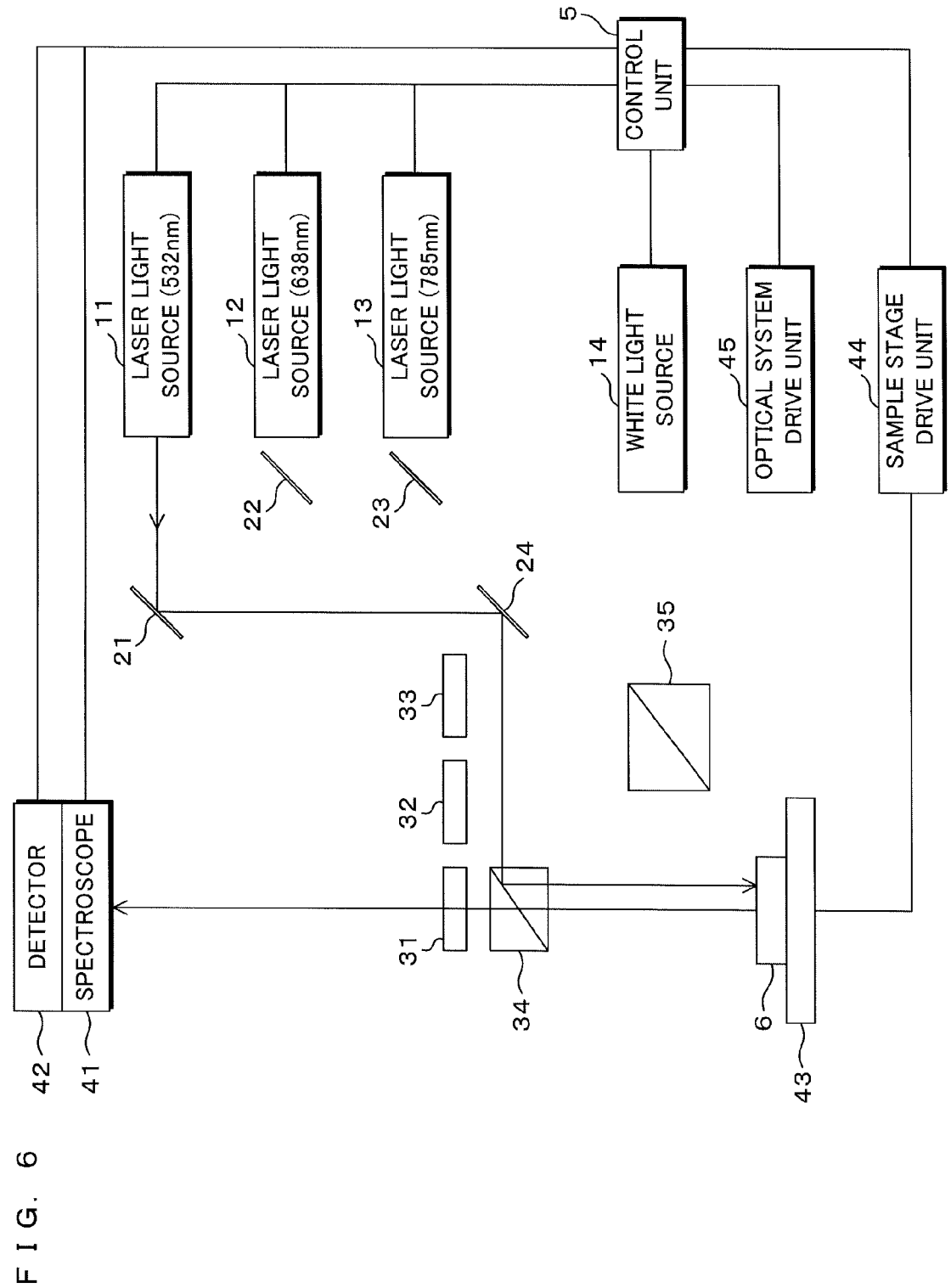
FIG. 6 is a block diagram illustrating a state of a colorant identification apparatus at the time of measuring a Raman spectrum.
Figure 7:
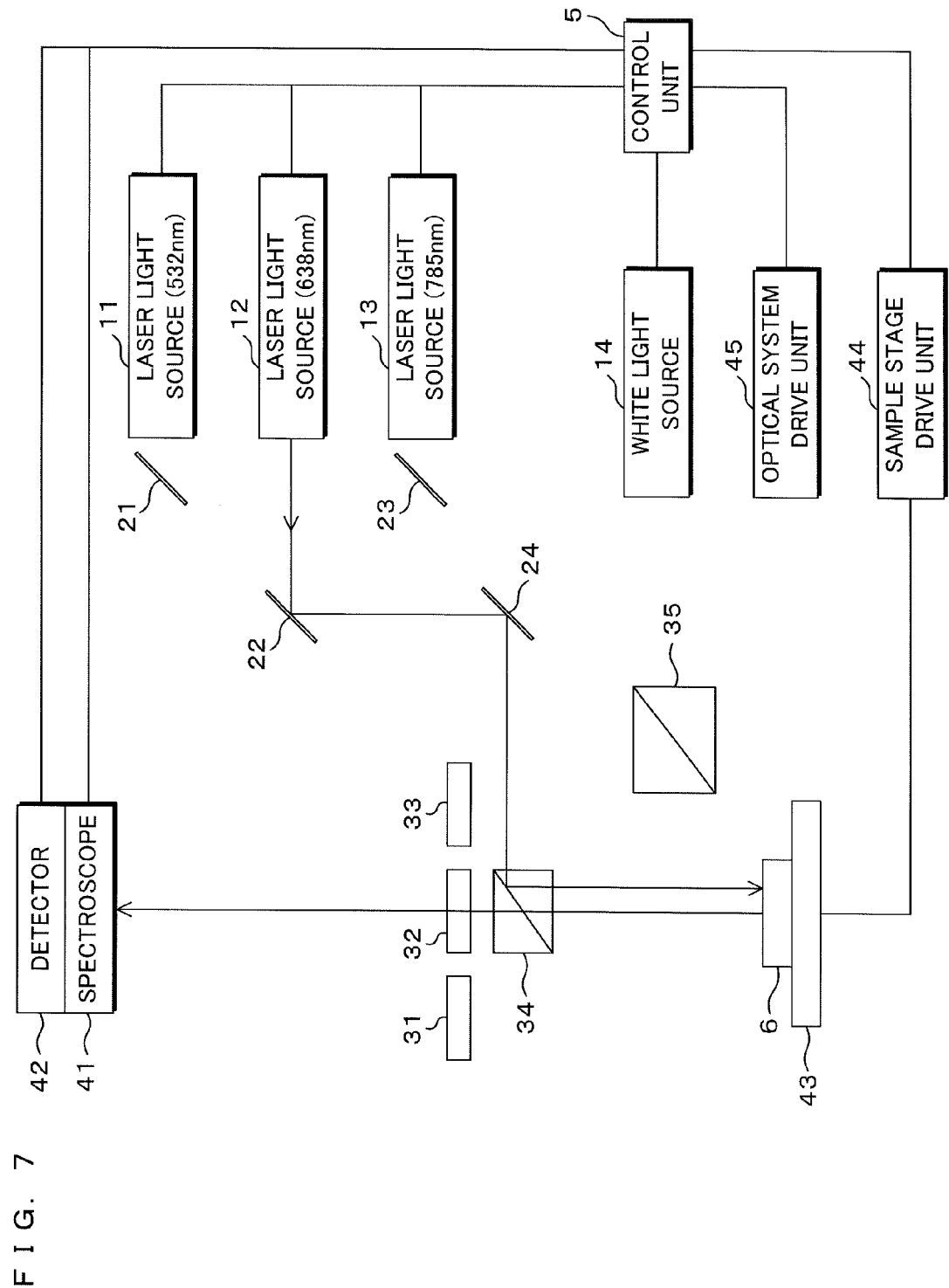
FIG. 7 is a block diagram illustrating a state of a colorant identification apparatus at the time of measuring a Raman spectrum.
Figure 8:
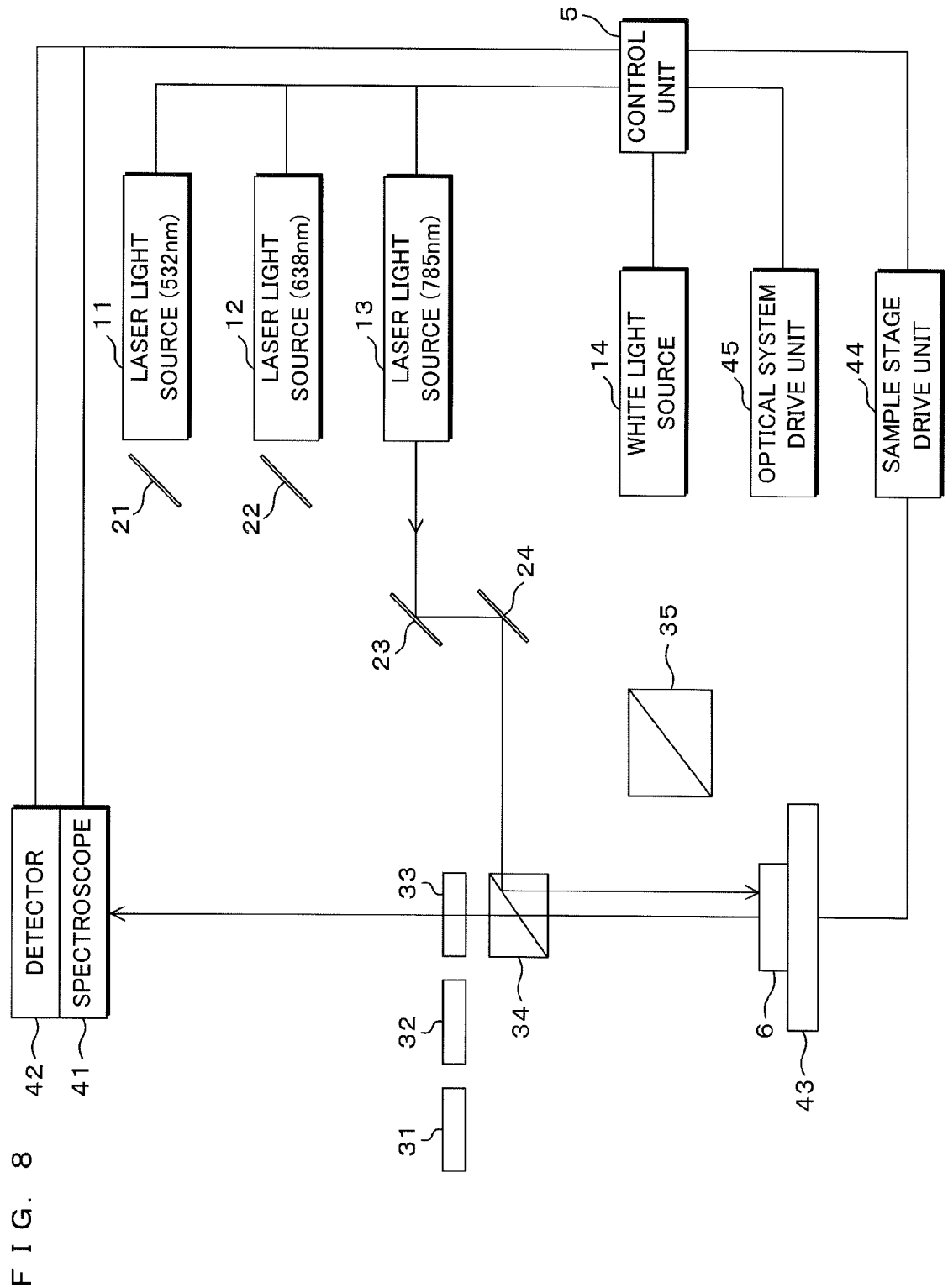
FIG. 8 is a block diagram illustrating a state of a colorant identification apparatus at the time of measuring a Raman spectrum.

Then, the colorant identification apparatus acquires a Raman spectrum from the single color portion of the sample 6 (S4). FIGS. 6, 7, and 8 are block diagrams illustrating the state of the colorant identification apparatus at the time of measuring the Raman spectrum. FIG. 6 illustrates an example of measurement of the Raman spectrum performed by using laser light of wavelength 532 nm. The control unit 5 controls the optical system drive unit 45 such that, as illustrated in FIG. 6, the beam splitter 34 and the Rayleigh cut filter 31 are arranged on the optical axis between the spectroscope 41 and the sample stage 43 and the mirror 21 is arranged at a position where laser light from the laser light source 11 is reflected toward the mirror 24. Further, when necessary, the control unit 5 adjusts the wavelength range of the spectroscopy performed by the spectroscope 41. The control unit 5 causes the laser light source 11 to emit light so that laser light of wavelength 532 nm is projected onto the sample 6. Then, Rayleigh scattered light and Raman scattered light are generated by the sample 6. The Rayleigh scattered light is cut off by the Rayleigh cut filter 31 and the Raman scattered light enters the spectroscope 41. FIG. 7 illustrates an example of measurement of the Raman spectrum performed by using laser light of wavelength 638 nm. As illustrated in FIG. 7, the control unit 5 arranges the Rayleigh cut filter 32 onto the optical axis and then arranges the mirror 22 at a position where laser light from the laser light source 12 is reflected toward the mirror 24. The control unit 5 causes the laser light source 12 to emit light. Then, laser light of wavelength 638 nm is projected onto the sample 6. Then, Rayleigh scattered light is cut off by the Rayleigh cut filter 32 and Raman scattered light from the sample 6 enters the spectroscope 41. FIG. 8 illustrates an example of measurement of the Raman spectrum performed by using laser light of wavelength 785 nm. As illustrated in FIG. 8, the control unit 5 arranges the Rayleigh cut filter 33 onto the optical axis and then arranges the mirror 23 at a position where laser light from the laser light source 13 is reflected toward the mirror 24. The control unit 5 causes the laser light source 13 to emit light. Then, laser light of wavelength 785 nm is projected onto the sample 6. Then, Rayleigh scattered light is cut off by the Rayleigh cut filter 33 and Raman scattered light from the sample 6 enters the spectroscope 41. In FIGS. 6, 7, and 8, the laser light and the Raman scattered light are indicated by arrows.

The control unit 5 uses laser light of the wavelength that is in correspondence to the colorant of the color of the single color portion in the wavelength data stored in the storage unit 54. For example, in the wavelength data, the wavelength of 532 nm is in correspondence to the black colorant, the wavelength of 638 nm is in correspondence to the cyan colorant, and the wavelength of 785 nm is in correspondence to the colorants of magenta and yellow. In this case, the control unit 5 uses laser light of wavelength 532 nm when the Raman spectrum of a black-colored portion is to be measured. When the Raman spectrum of a cyan-colored portion is to be measured, the laser light of wavelength 638 nm is used. When the Raman spectra of red- and yellow-colored portions are to be measured, laser light of wavelength 785 nm is used.

The control unit 5 controls the sample stage drive unit 44 so as to move the sample stage 43 horizontally and thereby adjust the position of the sample 6 such that laser light is projected onto the identified single color portion of the sample 6. Then, laser light of the wavelength corresponding to the colorant of the color of the single color portion is projected onto the single color portion of the sample 6. The detector 42 outputs a signal corresponding to the detected intensity of the Raman scattered light of each wavelength obtained by the spectroscopy. In a mode that the detector 42 is composed of a single channel detector, the control unit 5 controls the spectroscope 41 so as to sequentially change the wavelength of the Raman scattered light detected by the detector 42 and then the detector 42 sequentially outputs a signal corresponding to the detected intensity of the Raman scattered light whose wavelength is sequentially changed. On the basis of the contents of spectroscopy by the spectroscope 41 and the signal from the detector 42, the CPU 51 generates a Raman spectrum representing the relation between the Raman shift and the intensity of the Raman scattered light generated by the sample 6. Further, the control unit 5 measures the Raman spectrum in the single color portion identified for each of the colorants of plural colors. That is, the Raman spectrum is acquired in the single color portion of each of cyan, magenta, yellow, and black. Further, in a case that colorants of even the same color are related to mutually different wavelengths of laser light owing to the difference in the manufacturer, the control unit 5 projects, onto the same single color portion, laser light of the wavelengths individually corresponding to the plurality of manufacturers so as to individually measure the Raman spectra. The CPU 51 stores data representing the Raman spectrum in the storage unit 54.

Then, on the basis of the acquired Raman spectrum, the colorant identification apparatus identifies the colorant used in the sample 6 (S5). At step S5, the CPU 51 compares the acquired Raman spectrum with the Raman spectra of colorants of the equivalent color that represented by the Raman spectrum data stored in the storage unit 54. The colorant of the equivalent color is a colorant of a color having been set forth in advance to be the same color as the color of the single color portion in each manufacturer. For example, the Raman spectrum acquired in the yellow-colored portion is compared with the Raman spectra of the colorants of yellow fabricated from the individual manufacturers. The CPU 51 compares the acquired Raman spectrum with each of the Raman spectra of the individual manufacturers, thereby identifies a manufacturer having the closest Raman spectrum, and then performs the processing of identifying that the colorant used in the sample 6 is a colorant fabricated by the identified manufacturer. In a case that mutually different wavelengths of laser light need be used for measuring the Raman spectra owing to the difference of the manufacturers, the CPU 51 compares the Raman spectrum measured by using the laser light of the wavelength corresponding to each manufacturer with the Raman spectrum of the colorant of the manufacturer. Further, the CPU 51 performs identification on each of the colorants of plural colors whose Raman spectra have been measured. In a case that the colorants of plural colors are fabricated by mutually different manufacturers, the CPU 51 may adopt as an identification result the correspondence between each color and a manufacturer. Alternatively, when several manufacturers have been identified, a manufacturer having the largest number of times of being identified may be adopted as the final identification result. Further, in a case that plural kinds of colorants of the same color are present in the same manufacturer, the CPU 51 compares the acquired Raman spectrum with the Raman spectra of the plural kinds of colorants so as to identify the kind of the colorant. The CPU 51 store the identification result of the colorant in the storage unit 54 and then display the result on the display unit 56 when necessary.

Then, the colorant identification apparatus acquires distribution of the Raman spectrum on the sample 6 (S6). The control unit 5 controls the sample stage drive unit 44 so as to move the sample stage 43 horizontally and thereby projects laser light sequentially onto each portion of the sample 6 and generates sequentially a Raman spectrum from each portion of the sample 6. The CPU 51 establishes correspondence between the Raman spectrum in each portion of the sample 6 and each portion of the sample 6 and thereby acquires distribution of the Raman spectrum on the sample 6. With changing the wavelength of the laser light, the control unit 5 acquires distribution of the Raman spectrum for each wavelength. The CPU 51 stores data representing the distribution of the Raman spectrum in the storage unit 54. Then, the colorant identification apparatus terminates the processing. Here, the colorant identification apparatus may be in a mode that acquisition of the distribution of the Raman spectrum is omitted.

As described above in detail, in the present embodiment, on the basis of the distribution of the reflectance spectrum and the fluorescence emission spectrum in a color image, the colorant identification apparatus identifies a single color portion generated with only one colorant and then identifies the colorant on the basis of the Raman spectrum of the single color portion. As for the colorant of single color in which other colorants are not mixed in, it is easy to prepare standard Raman spectra for individual manufacturers. In the Raman spectrum of a single color portion generated with only one colorant among the colorants of plural colors, the Raman spectra of other colors are not superposed thereon. Thus, the difference in the spectrum is attributed to the difference in the composition depending on the manufacturer. Thus, when the Raman spectrum of the single color portion is compared with the standard Raman spectra of the equivalent color prepared in advance for individual manufacturers, the manufacturer of the colorant is identified and hence the colorant is identified easily. Thus, an image forming apparatus used in generation of unauthorized image recorded matter in which a color image is recorded is allowed to be identified, and this provides information useful in investigation of the circumstances of generation of the unauthorized image recorded matter.

Further, fluorescence emission spectra corresponding to the colors are obtained from a color image. Thus, when the measured fluorescence emission spectra are compared with the standard fluorescence emission spectra, a single color portion contained in the color image is allowed to be identified from the distribution of the fluorescence emission spectrum. In the color image, a portion is present that looks like a color equivalent to one colorant but actually is generated with a mixture of colorants of plural colors. However, since the fluorescence emission spectrum of a colorant of single color is different from the fluorescence emission spectrum of a mixture of colorants of plural colors, a single color portion is allowed to be identified in the color image. The Raman spectrum of a mixture of colorants of plural colors is obtained by superposing the Raman spectra of the colorants of single colors with each other. Instead, the fluorescence emission spectrum of a mixture of colorants of plural colors is different from that obtained by superposing the Raman spectra of the colorants of single colors with each other. Thus, in the fluorescence emission spectrum, the difference between a colorant of single color and a mixture of colorants of plural colors becomes remarkable. Accordingly, for the purpose of identification of a single color portion, the fluorescence emission spectrum is more useful than the Raman spectrum. Strictly, colorants of even the same color have slightly different fluorescence emission spectra with each other when their manufacturers are different from each other. However, the difference of the fluorescence emission spectra caused by the difference of colors and the difference of the fluorescence emission spectra between a colorant of single color and a mixture of colorants of plural colors are remarkable. This permits the specification of a single color portion. In the present embodiment, by using the distribution of the reflectance spectrum, a region containing the reflectance spectrum of a color equivalent to a colorant of single color is identified and then a single color portion is identified from the identified region on the basis of the fluorescence emission spectrum. This permits accurate identification of the single color portion.

Further, as described above, a suitable wavelength of laser light to be used in measurement of the Raman spectrum has been set forth for each colorant. In the present embodiment, the colorant identification apparatus stores in advance the relation between the wavelength of laser light and the Raman spectrum. Thus, when the Raman spectrum measured by using the laser light of the particular wavelength is compared with the standard Raman spectra corresponding to the particular wavelength, the colorant is allowed to be identified accurately. Further, in the present invention, each of the colorants of plural colors used in generating a color image is identified. When the identification result of the largest number of times of being identified is adopted as the final identification result, the colorant is allowed to be identified more accurately. Alternatively, a combination of the identification results of colorants of plural colors is allowed to be used as information more useful in investigation of the circumstances of generation of unauthorized image recorded matter. Further, in the present embodiment, the colorant identification apparatus acquires the distribution of the Raman spectrum. When the distribution of the Raman spectrum is acquired, the distribution of the colorant of each color is obtained and this provides useful further information such as the amount of usage of the colorant of each color.

Here, the present embodiment has been described for a mode of identifying a colorant of single color which is one of colorants of plural colors used in generating a color image. Instead, the colorant identification apparatus may be in a mode of identifying a mixture of colorants obtained by mixing colorants of plural colors at a particular ratio. Also in this mode, when data representing the fluorescence emission spectra and the Raman spectra of mixtures of colorants obtained by mixing the colorants of plural colors at particular ratios is stored in advance in the storage unit 54, identification of the colorant is allowed.

Further, the present embodiment has been described for a mode that the optical axis of projection of white light and laser light onto the sample 6 and the optical axis of the reflected light, the fluorescence, and the Raman scattered light from the sample 6 are aligned with each other. Instead, the colorant identification apparatus may be in another mode implemented by another optical system like the above-mentioned optical axes are separated from each other. Further, the present embodiment has been described for a mode that laser light of wavelengths 532 nm, 638 nm, and 785 nm is employed. Instead, the colorant identification apparatus may be in a mode that laser light of other wavelengths is employed. Further, the colorant identification apparatus may be in a mode that monochromatic light other than laser light is employed. Further, the colorant identification apparatus may be in a mode that the distribution of the reflectance spectrum, the fluorescence emission spectrum, and the Raman spectrum is acquired without the necessity of moving the sample stage 43, for example, by a method of moving the optical path of the laser light. Further, the present embodiment has been described for a mode that the processing of measurement of the reflectance spectrum, measurement of the fluorescence emission spectrum, measurement of the Raman spectrum, and identification of the colorant is executed by a single apparatus. Instead, the present invention may be implemented by using a plurality of measurement devices and analyzing instruments. Alternatively, a part of the processing may be executed by manual operation of a user. Further, in the present invention, the colorant may be identified without using the reflectance spectrum.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A colorant identification method for identifying a colorant used in generating a color image, comprising steps of:
    storing in a database a fluorescence emission spectrum of a colorant of particular color and Raman spectra of plural kinds of colorants of a color which is equivalent to the particular color and of different compositions;
    projecting a monochromatic light onto a color image, then measuring fluorescence generated in each portion of the color image, and thereby acquiring distribution of a fluorescence emission spectrum in the color image;
    from the acquired distribution of the fluorescence emission spectrum, identifying a portion containing a fluorescence emission spectrum which is equivalent to the fluorescence emission spectrum of the colorant of the particular color stored in the database and thereby identifying a portion of the color image corresponding to the portion identified from the acquired distribution of the fluorescence emission spectrum;
    projecting monochromatic light onto the identified portion of the color image and thereby acquiring a Raman spectrum; and
    comparing the acquired Raman spectrum with the Raman spectra stored in the database and thereby identifying the colorant.

2. The colorant identification method according to claim 1, further comprising steps of:
    projecting white light onto the color image, then measuring reflected light from the color image, and thereby acquiring distribution of a reflectance spectrum in the color image;
    from the acquired distribution of the reflectance spectrum, identifying a region containing a reflectance spectrum corresponding to the particular color; and
    from a portion in the distribution of the fluorescence emission spectrum corresponding to the identified region, identifying a portion containing a fluorescence emission spectrum which is equivalent to the fluorescence emission spectrum of the colorant of the particular color.

3. The colorant identification method according to claim 1, further comprising steps of:
    storing in advance a wavelength of monochromatic light necessary for acquiring the Raman spectrum in the database in a manner of being in correspondence to each of the Raman spectra of the plural kinds of colorants;
    projecting monochromatic light of the wavelength stored in the database onto the color image and thereby acquiring a Raman spectrum; and
    comparing the Raman spectrum acquired by using monochromatic light of the particular wavelength with the Raman spectrum stored in correspondence to the particular wavelength in the database, and thereby identifying the colorant.

4. The colorant identification method according to claim 1, wherein the colorant of the particular color is one of colorants of plural colors used in generating a color image.

5. The colorant identification method according to claim 4, further comprising a step of
    identifying the colorant for each of the plural colors.

6. The colorant identification method according to claim 1, further comprising a step of
    measuring Raman scattered light generated in each portion of the color image and thereby acquiring distribution of a Raman spectrum in the color image.

7. A colorant identification apparatus for identifying a colorant used in generating a color image, comprising:
    a monochromatic light source;
    a storage unit storing a fluorescence emission spectrum of a colorant of particular color and Raman spectra of plural kinds of colorants of a color which is equivalent to the particular color and of different compositions;
    a fluorescence emission spectrum distribution acquisition unit projecting monochromatic light from the monochromatic light source onto a color image, then measuring fluorescence generated in each portion of the color image, and thereby acquiring distribution of a fluorescence emission spectrum in the color image;

a first identification unit, from the distribution of the fluorescence emission spectrum acquired by the fluorescence emission spectrum distribution acquisition unit, identifying a portion containing a fluorescence emission spectrum which is equivalent to the fluorescence emission spectrum of the colorant of the particular color stored in the storage unit, and then identifying a portion of the color image corresponding to the portion;

a Raman spectrum acquisition unit projecting monochromatic light onto the portion of the color image identified by the first identification unit and thereby acquiring a Raman spectrum; and an identification unit comparing the Raman spectrum acquired by the Raman spectrum acquisition unit with the Raman spectrum stored in the storage unit and thereby identifying the colorant.

8. The colorant identification apparatus according to claim 7, further comprising:

a white light source;

a reflectance spectrum distribution acquisition unit projecting white light from the white light source onto the color image, then measuring reflected light from the color image, and thereby acquiring distribution of a reflectance spectrum in the color image; and a second identification unit, from the distribution of the reflectance spectrum acquired by the reflectance spectrum distribution acquisition unit, identifying a region containing a reflectance spectrum corresponding to the particular color, wherein from a portion in the distribution of the fluorescence emission spectrum corresponding to the region identified by the second identification unit, the first identification unit identifies a portion containing a fluorescence emission spectrum which is equivalent to the fluorescence emission spectrum of the colorant of the particular color.

* * * * *